United States Patent
Masuda et al.

[11] Patent Number: 5,578,664
[45] Date of Patent: Nov. 26, 1996

[54] METHODS OF SOLUBILIZING IODINE IN AQUEOUS MEDIUM AND AQUEOUS ANTISEPTIC COMPOSITION CONTAINING IODINE

[75] Inventors: Mitsutoshi Masuda; Yukimichi Nakao; Toshimi Shimizu, all of Tsukuba, Japan

[73] Assignee: Director-General Of Agency Of Industrial Science & Technology, Japan

[21] Appl. No.: 524,041

[22] Filed: Sep. 6, 1995

[30] Foreign Application Priority Data

Sep. 9, 1994 [JP] Japan .................... 6-216269

[51] Int. Cl.$^6$ ............... C08K 3/02; C08L 25/18
[52] U.S. Cl. ............................. 524/80; 524/543
[58] Field of Search ......................... 524/80, 543

[56] References Cited

U.S. PATENT DOCUMENTS

| | | | |
|---|---|---|---|
| 3,190,925 | 6/1965 | Stowe | 526/289 |
| 4,287,319 | 9/1981 | Phillips | 524/80 |
| 4,610,811 | 9/1986 | Yamamoto et al. | 524/80 |
| 5,242,985 | 9/1993 | Shih et al. | 524/80 |

FOREIGN PATENT DOCUMENTS

| | | | |
|---|---|---|---|
| 0117927 | 5/1990 | Japan | 524/80 |

*Primary Examiner*—Peter A. Szekely
*Attorney, Agent, or Firm*—Lorusso & Loud

[57] ABSTRACT

A method of solubilizing iodine in an aqueous medium is disclosed, which includes mixing the aqueous medium with iodine together with a polystyrene derivative having the recurring units of the formula

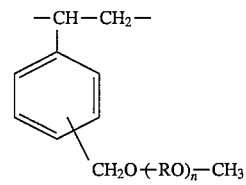

wherein R represents an alkylene group having 1–4 carbon atoms and n is an integer of 2–20. An antiseptic composition includes an aqueous medium, the above polystyrene derivative, and iodine dissolved in the aqueous medium.

7 Claims, No Drawings

METHODS OF SOLUBILIZING IODINE IN AQUEOUS MEDIUM AND AQUEOUS ANTISEPTIC COMPOSITION CONTAINING IODINE

BACKGROUND OF THE INVENTION

This invention relates to a method of solubilizing iodine in an aqueous medium and to an antiseptic composition containing iodine dissolved in an aqueous medium.

Because of its aseptic action, iodine has been used for various applications such as germicides and antiseptics. Since, however, iodine is hardly soluble in water (solubility: 0.29 g/1000 ml at 20° C.), it is necessary to use a solubilizer to form an aqueous iodine solution. Known such solubilizers include polyvinyl alcohol and poly(vinyl pyrrolidone). These solubilizers should be used in conjunction with an alkali metal iodide, such as KI, serving as an auxiliary agent or an stabilizer.

U.S. Pat. No. 3,190,925 discloses a monomer having the formula:

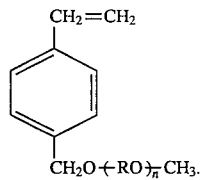

The monomer is used for forming a copolymer which is utilized as an additive for synthetic textile fibers in the capacity of anti-static agents, humectant dye-receptors or stabilizers. The monomer is described to be usable for forming homopolymers.

SUMMARY OF THE INVENTION

The present invention provides a method of solubilizing iodine in an aqueous medium, which includes mixing the aqueous medium with iodine together with a polystyrene derivative having the recurring units of the formula (I):

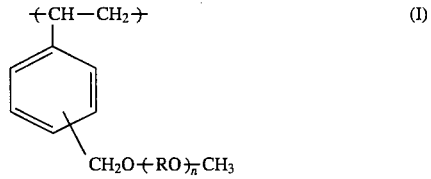

wherein R represents an alkylene group having 1–4 carbon atoms and n is an integer of 2–20.

The present invention also provides a composition of matters which includes an aqueous medium, a polystyrene derivative having the recurring units of the formula (I):

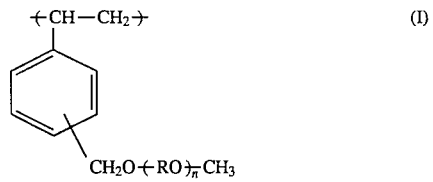

wherein R represents an alkylene group having 1–4 carbon atoms and n is an integer of 2–20, and iodine dissolved in the aqueous medium.

Although not wishing to be bound to such a theory, it is believed that the iodine in the solubilized state according to the present invention is included in a hydrophobic region of the molecules of polystyrene derivative in the form similar to $I_3^-$ ($\lambda_{max}$: 350 nm) in view of the fact that the aqueous solution containing iodine and the polystyrene derivative has a $\lambda_{max}$ of about 380 nm.

In one embodiment, the method of the present invention may be utilized for fixing iodine. For example, iodine vapors formed during the industrial production of iodine can be suitably trapped and collected according to the method of the present invention. The thus captured iodine may be liberated by heating the iodine-containing aqueous medium and thus may be recovered. The thus regenerated aqueous medium may be again used for absorbing iodine. Further, iodine formed in situ in a gas or liquid medium may be fixed according to the method of the present invention.

It is an object of the present invention to provide a method which can solubilize iodine in an aqueous medium without using an adjuvant or stabilizer such as KI.

Another object of the present invention is to provide a method of the above-mentioned type in which a large amount of iodine can be solubilized with a small amount of a solubilizer.

It is a further object of the present invention to provide an antiseptic composition such as a germicide, a gargle or an eyewash.

It is a special object of the present invention to provide a method of fixing iodine contained in an atmosphere or formed in situ in a fluid.

Other objects, features and advantages of the present invention will become apparent from the detailed description of the preferred embodiments to follow.

DETAILED DESCRIPTION OF THE PREFERRED EMBODIMENTS OF THE INVENTION

The present invention uses a polystyrene derivative having the recurring units of the above formula (I) as a solubilizer for iodine. In the formula (I), R is preferably —$CH_2$—, —$CH_2CH_2$—, —$CH_2CH_2CH_2$— or —$CH_2CH_2CH_2CH_2$— and n is preferably 2–17, more preferably 3–12. The polystyrene derivative preferably has a number average molecular weight of $3\times10^3$ to $1\times10^6$, more preferably $1\times10^4$ to $2\times10^5$.

The polystyrene derivative of the formula (I) may be prepared in any known manner, such as by radical polymerization, using a monomer of the formula (II):

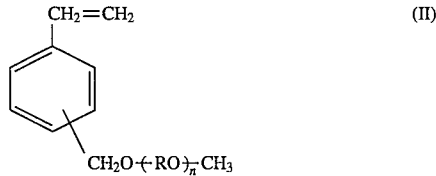

herein R and n are as defined above. The —$CH_2O$($RO$)$_n$$CH_3$ group of the monomer of the formula (II) is generally located at para- or meta-position relative to the vinyl group. The monomer is polymerized at a temperature of 40°–100° C. and a pressure of 0.1–3 atm for 2–30 hours in the presence of a suitable polymerization initiator such as an azo compound or an organic peroxide using a solvent such as toluene, chloroform, benzene or water.

The monomer (II) may be suitably obtained by the following reactions using tetrahydrofuran as a solvent (Ph: phenylene ):

HO(C₂H₂O)ₙCH₃+NaH→NaO(C₂H₂O)ₙCH₃+
H₂NaO(C₂H₂O)ₙCH₃+CH₂=CH—Ph—CH₂Cl→
CH₂=CH—Ph—CH₂O (C₂H₂O ₙCH₃

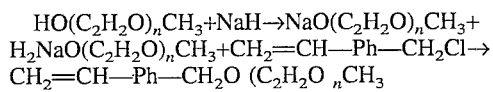

In solubilizing iodine in an aqueous medium, the polystyrene derivative is preferably used in an amount of 0.1–3 parts by weight, more preferably 0.5–2 parts by weight, per part by weight of the iodine. According to the present invention, an iodine containing aqueous solution having generally up to 5% by weight preferably up to 2% by weight may be obtained.

The following examples will further illustrate the present invention.

EXAMPLE

Preparation of Polystyrene Derivatives:

Into 20 ml of toluene was dissolved 0.01 mole of each of the monomers having the formula (III) below:

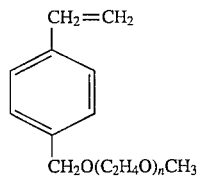

wherein n is 2, 3, 4, 7, 12 or 17. After addition of 0.0061 g of azobisisobutylonitrile (polymerization initiator), the solution was polymerized at 60° C. for 24 hours under ambient pressure. The reaction solution was poured in 0.5 liter of n-hexane to precipitate a polymer. The polymer was separated by decantation, washed with n-hexzane and dried. The thus obtained polystyrene derivatives had the structure shown by the formula (I) and the number average molecular weights shown in Table below.

Preparation of Aqueous Iodine Solutions:

Each of the polystyrene derivatives was dissolved in water to form 5 kinds of the aqueous polymer solutions having a concentration of the polystyrene derivative of 0.2, 0.4, 0.6, 0.8 and 1% by weight. Using each of the aqueous polymer solutions, iodine was dissolved to form aqueous iodine solutions. The solubility (amount (g) of iodine dissolved in 1 liter of the polymer solution) of iodine at 20° C. in each of the polymer solutions is shown in Table below. The solubility of iodine in pure water (polymer concentration: 0%) was 0.29 g/l.

TABLE

Solubility (g) of Iodine in 1 liter of Polymer Solution

| Polystyrene Derivative | | Concentration of Polystyrene Derivative in Polymer Solution (% by weight) | | | | |
|---|---|---|---|---|---|---|
| n | MW (×10⁴) | 0.2 | 0.4 | 0.6 | 0.8 | 1.0 |
| 2 | 7 | 1.2 | 2.3 | 3.2 | 4.2 | 5.3 |
| 3 | 5 | 1.3 | 2.7 | 3.8 | 5.0 | 6.4 |
| 4 | 3 | 1.2 | 2.3 | 3.3 | 4.4 | 5.6 |
| 7 | 6 | 0.90 | 1.9 | 2.6 | 3.5 | 4.61 |
| 12 | 4 | 0.77 | 1.6 | 2.2 | 2.8 | 3.8 |
| 17 | 8 | 0.63 | 1.3 | 1.8 | 2.42 | 3.1 |

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A method of solubilizing iodine in an aqueous medium, comprising mixing said aqueous medium with iodine together with a polystyrene derivative having the recurring units of the formula:

$$-CH-CH_2-$$
$$\underset{\underset{CH_2O(RO)_n-CH_3}{|}}{\bigcirc}$$

wherein R represents an alkylene group having 1–4 carbon atoms and n is an integer of 2–20.

2. A method according to claim 1, wherein said polystyrene derivative has a number average molecular weight of 3×10³ to 1×10⁶.

3. A method according to claim 1, wherein said polystyrene derivative has a number average molecular weight of 1×10⁴ to 2×10⁵.

4. A method according to claim 1, wherein n is an integer of 3–12.

5. A method according to claim 1, wherein the amount of said polystyrene derivative is 0.1–3 parts by weight per part by weight of said iodine.

6. A method according to claim 1, wherein said recurring unit has the following formula:

$$-CH-CH_2-$$
$$\underset{\underset{CH_2O(RO)_n CH_3}{|}}{\bigcirc}$$

wherein R and n are as defined above.

7. A composition of matters comprising an aqueous medium, a polystryene derivative having the recurring units of the formula:

$$-CH-CH_2-$$
$$\underset{\underset{CH_2O(RO)_n CH_3}{|}}{\bigcirc}$$

wherein R represents an alkylene group having 1–4 carbon atoms and n is an integer of 2–20, and iodine dissolved in said aqueous medium.

* * * * *